United States Patent [19]

Stiles

[11] Patent Number: 4,562,174

[45] Date of Patent: Dec. 31, 1985

[54] CATALYST FOR THE PRODUCTION OF ALKANOLS

[75] Inventor: Alvin B. Stiles, Wilmington, Del.

[73] Assignee: Alberta Gas Chemicals Ltd., Edmonton, Canada

[21] Appl. No.: 612,633

[22] Filed: May 21, 1984

[51] Int. Cl.[4] .......................... B01J 23/72; B01J 23/78; B01J 23/80; B01J 23/84

[52] U.S. Cl. .................................. 502/174; 502/241; 502/245; 502/302; 502/303; 502/304; 502/324; 502/329; 518/713

[58] Field of Search ............... 502/174, 241, 243, 307, 502/324, 329, 342, 343, 302, 303, 304, 245; 518/713

[56] References Cited

U.S. PATENT DOCUMENTS 3,790,505  2/1974  Casey et al. ...................... 502/342

4,107,089  8/1978  Bondar et al. ...................... 502/307

FOREIGN PATENT DOCUMENTS 3005551  8/1981  Fed. Rep. of Germany ...... 502/342
2037179  7/1980  United Kingdom .

Primary Examiner—W. J. Shine
Attorney, Agent, or Firm—Charles E. Baxley

[57] ABSTRACT

The inclusion of salts of rubidium or cesium or mixtures thereof in a catalyst comprised of copper and zinc oxides and optionally manganese oxide or manganese and cobalt oxides and a stabilizer such as chromic, ceric, magnesium or aluminum oxides results in higher yields of $C_1$ to $C_6$ alkanols and lower production of hydrocarbons in the effluent from the catalytic reaction environment. The reactant gases passing over the catalyst comprises hydrogen and carbon monoxide and optionally carbon dioxide if economically advantageous.

25 Claims, No Drawings

CATALYST FOR THE PRODUCTION OF ALKANOLS

This invention relates to the preparation of alkanols. It particularly relates to vapor-phase process for the preparation of alkanols containing from one to six carbon atoms by reacting a gaseous mixture comprising hydrogen and carbon monoxide and optionally carbon dioxide and a catalyst composition for use in the process.

BACKGROUND OF THE INVENTION

The production of alcohols from synthesis gas, the common designation for mixtures of hydrogen, carbon monoxide and carbon dioxide, is a process which has been practiced since the early twentieth century. German inventors Mittasch, Schneider, Winkler, Fischer, Tropsch during the period 1915 through 1930 made many inventions relating to the production of methanol and hydrocarbons from carbon monoxide, hydrogen and carbon dioxide. These early processes differed very significantly from the more efficient, more specific processes of the present. For example, Davies et al., in U.S. Pat. No. 3,326,956 teach the manufacture of almost pure methanol from CO and hydrogen plus carbon dioxide using a copper oxide, zinc oxide and aluminum oxide catalyst. Furthermore, Stiles in U.S. Pat. No. 4,111,847 taught the preparation of methanol also from synthesis gas increasing the rate of production per unit volume of catalyst and minimizing the production of unwanted by-products such as methane, hydrocarbons and higher alcohols.

Presently, it is desirable to produce methanol together with selected and specific higher alcohols from CO and hydrogen in order to produce an alcohol mixture which can be added to gasolines to make the United States less dependent upon foreign crude imports as well as to improve the gasoline's anti-knock properties. When methanol in its pure form is added to gasoline there are many complications which can develop such as water being adsorbed by the gasoline and forming a two-phase layer in the gasoline tanks. This causes extreme motor and driving problems.

However, if there are present in the methanol which is added to the gasoline quantities of 10 to 50% of higher alcohols including ethanol, propanol and butanols then this separation of phases is not a problem. As a consequence much work has recently been done in an effort to simultaneously produce methanol and these selected higher alcohols. For example, Sugier et al., in U.S. Pat. No. 4,122,110 teach the use of a catalyst comprising copper, cobalt and optionally chromium, manganese, vanadium or iron and an alkali metal. The alkali metal is preferably lithium, sodium or potassium. The product of the synthesis includes methanol, ethanol, propanol, isopropanol and butanols. A companion patent GB No. 2,037,179 was granted in Great Britian which claims essentially the same features of the catalyst with the exception that alkali earths are included as an equivalency for the lithium, sodium and potassium. No mention is made of cesium or rubidium or mixtures of the foregoing with cesium and rubidium.

Bartley et al., in U.S. Pat. No. 4,235,798 teach a process whereby synthesis gas is converted to two carbon atom products such as ethanol, ethylene glycol and acetaldehyde using a catalyst comprising rhodium, lithium, potassium, cesium, or rubidium on $SiO_2$. This process is extremely inefficient in that the quantities of methane which are simultaneously produced are equal to 22% up to 56% of the total carbon monoxide fed. Thus this is an extremely inefficient process and although it stipulates cesium and rubidium as alkali it contains none of the other typical ingredients of alcohols synthesis catalyst such as copper, zinc manganese, and alumina.

In another process for producing higher alcohols Universal Oil Products in British patent GB No. 2,049,673 teach the reacting of olefinic materials with CO and hydrogen using group 8 metals as catalysts. These metals of course include the iron group and the platinum group but no mention is made of the use of alkali metals to moderate the reaction.

Ball et al., in U.S. Pat. No. 4,327,190 teach the synthesis of oxygenated compounds from synthesis gas using a catalyst comprising rhodium and chromium on silica gel. No alkali is included in the catalyst composition. Snamprogetti teach in British Pat. No. 2,083,469 the conversion of synthesis gas to mixtures of methanol and higher alcohols. The catalyst employed in this reaction is zinc and chromium plus alkali metal which is taught to be preferably potassium. Hardman et al., teach in U.S. Pat. No. 4,298,354 that synthesis gas can be converted to methanol and higher alcohols over a catalyst comprising copper, thorium oxide and alkali metal with the alkali metal being preferably sodium.

It can be seen that there is much prior patent art in this field but cesium or rubidium are not mentioned in any sense approaching the disclosures of the invention taught herein.

Despite the foregoing background indicating the degree to which this subject has been exposed to research world-wide, there exist problems which must be corrected. One of the problems is the concomitant production of relatively large quantities of methane. The loss of valuable synthesis gas to methane is in itself a serious economic loss but it becomes even more serious when purging of the methane from the synthesis system. During the purging of this objectionable methane there is lost simultaneously at least the equivalent of two additional volumes and very likely more of valuable CO and hydrogen. Thus it becomes apparent that avoidance of methanation is an extremely critical item and is the subject of one of the improvements of the catalysts of of this invention. Furthermore, it is highly desirable to produce only those products which will be most effectively used when blending methanol and higher alcohols into the gasoline fraction. The invention later to be described will also achieve this characteristic. In other words, the present invention differs from the previously described prior art in that the new catalysts have compositions which differ from anything previously described, produce less methane and also produce larger quantities of higher alcohols of the desired identity.

THE DESCRIPTION OF THE INVENTION

It is an object of this invention to provide a vapor-phase process for the production in good yield of $C_1$ and $C_6$ alkanols from gaseous compositions comprising hydrogen and carbon monoxide and optionally carbon dioxide.

It is another object of this invention to improve the efficiency of the process so that little or no concommitant production of methane and other hydrocarbons occurs.

It is a further object of this invention to provide a catalyst composition for use in the process which has good thermal stability and resistance to poisoning by sulfur, halogens and other possible contaminants. It is still another object of this invention to provide a process for the preparation of the $C_1$–$C_6$ alcohols without the production of unwanted other hydrocarbons or organic acids.

It is still another object of this invention to provide a catalytic process for the preparation of oxygenated compounds such as aldehydes and ketones simultaneously with the alcohols and which compounds have high commercial value. However if it is desired to convert these to alcohols to give a 100% alcohol product, a simple hydrogenation step can be performed to accomplish this.

In accordance with this invention there is provided a vapor-phase process and catalysts therefor for the preparation of $C_1$ and $C_6$ alcohols which comprises passing a feed gas composed of hydrogen, carbon monoxide and optionally carbon dioxide over a catalyst the composition of which is described below at a temperature from about 350° F. to about 850° F. preferably from about 600° to about 780° F. and at pressures from about 1000 to about 5000 psi preferably from about 1200 to about 3500 psi.

The feed gas contains in percent by volume from about 1 to about 99, preferably from about 67 to 96 of hydrogen and from about 99 to 1 preferably about 33 to about 4 of carbon monoxide. In addition to these gases it may be desirable for operating or economic reasons to have in the feed gas other gases such as carbon dioxide and relatively inert gases such as nitrogen, methane and others. When carbon dioxide is a constituent, the feed gas may contain from about 0.5 to about 20% by volume of carbon dioxide and a preferred feed gas contains in percent by volume about 60–90% of hydrogen from about 10 to about 33% of carbon monoxide and from about 0 to about 10% of carbon dioxide.

The space velocity, which is the volume of gas at standard temperature and pressure (0° C. at 1 atmospheric pressure) passed over the catalyst per hour divided by the volume of the catalyst, may range from about 5,000 to about 50,000 and is preferably about 40,000 although at elevated pressures it may beneficially exceed 50,000. It is noteworthy that a secondary control of higher alcohol production in addition to the alkali metal or metals salts is the absence of or quantity of carbon dioxide in the feed gas. This must be optimized as to catalyst composition and temperature, pressure and space velocity of operation. In accordance with this invention it has been found that the addition of an alkali metal salt or hydroxide to a catalyst composition containing a stabilizer described below serves to promote the yield of $C_2$ to $C_6$ alkanols and simultaneously decreases or eliminates hydrocarbons and minimizes methanation.

A catalyst for use in the practice of this invention is comprised of (1) a mixture of the oxides of copper, zinc and cobalt which mixture may optionally contain manganese oxide; (2) a stabilizer selected as one or more from the group consisting of the oxides, hydroxides or carbonates of aluminum, chromium, alkaline earths, lanthanides, tantalum, niobium, silica, zirconium, titanium, thorium, uranium, yttrium, and (3) at least one alkali metal salt or hydroxide with the proviso that at least one of said salts be of either rubidium or cesium.

Preferably a mixture of the oxides of copper, zinc, manganese and cobalt is used. The respective atomic ratios of the metals as oxides in the mixture may range from about 0.1 to about 4.0. Preferred compositions contain copper oxide, zinc oxide and manganese oxide and cobalt oxide in the respective ratios of 2:2:2:0.25 and 4:1:3:0.025. The latter catalyst favors the production of alkanols containing from 1 to 4 carbon atoms.

The stabilizer may consist of one or more of the compounds listed above. Suitable alkaline earth metal compounds include the oxides and carbonates of magnesium, calcium, strontium, and barium. The catalyst composition may contain from about 1 to 50% preferably from 2 to 14% by weight of stabilizer. As pointed out above, the alkaline earths have an additional function and that is of acting as a promoter or a moderator for the catalyst.

The alkali metal salt may be of lithium, sodium, potassium, rubidium or cesium and is present in the catalyst composition in an amount ranging from about 0.1 to about 10%, preferably from about 1 to 7% by weight. Suitable salts include carbonates, bicarbonates, premanganates, sulfates, chromates, phosphates, silicates, oxalates, nitrates, formates, acetates and the like. The carbonates are preferred and the preferred catalyst composition contains rubidium carbonate or cesium carbonate or a mixture of either potassium and rubidium carbonate or potassium and cesium carbonates or rubidium and cesium carbonates or rubidium, cesium and potassium carbonates.

The invention will become clearer from the examples and the tables which follow. The examples and the data contained in the tables are given for an illustrative purpose and are not to be considered limiting.

EXAMPLE 1

This example is not the preferred composition of this application but reveals the degree to which alkali metals can alter the performance of what is otherwise a specific methanol synthesis catalyst. The composition described in this example consists of the oxides of copper, zinc and aluminum with the aluminum oxide serving as stabilizer. Rubidium was subsequently added to one portion of this catalyst to demonstrate the effectiveness of rubidium in producing higher alcohols even from a very specific methanol synthesis catalyst. The catalyst was prepared as follows: an aqueous solution containing copper, zinc and aluminum was prepared by dissolving 70 parts by weight of zinc nitrate trihydrate, 300 parts by weight of copper nitrate trihydrate and 180 parts by weight of aluminum nitrate nonahydrate in 1500 parts by weight of distilled water at about 30±1° C.

To this solution maintained at 30±1° C. a 10% aqueous solution of sodium bicarbonate also maintained at 30±1° C. was added with rapid stirring until the pH of 7.0±0.1 was reached and a precipitate had formed. The slurry was agitated gently for an additional hour and then filtered. The filter cake was washed with 1000 parts of distilled water and dried.

The dried, filter cake was heated to 400° C.±10° C. and then calcined for about two hours at this temperature.

Since sodium nitrate which is harmful to catalysts had been occluded to some degree by the precipitated catalyst and the calcining had released most of the occluded alkali, the calcined catalyst was washed with an ion exchange solution to remove the sodium nitrate. This was accomplished by slurrying the finely divided calcined catalyst in 2000 parts of a 0.1% aqueous ammonium bicarbonate solution and agitated for about 10 minutes. The stirring was stopped and the precipitate allowed to settle. The supernatant liquid was decanted and replaced by an equal volume of 0.1% aqueous ammonium bicarbonate solution and the above steps continued.

This treatment was repeated until the supernatant liquid was free of sodium ion as indicated by spectrographic analysis. The precipitate was then filtered and the filter cake dried. The dried filter cake was granulated so 100% passed through a 10-mesh screen.

If the powder had an apparent density exceeding 0.6 g/ml it was mixed with 1.0% graphite powder and then pilled. If the powder had an apparent density of below 0.6 it was kneaded to increase the density so that the apparent density after granulation was above 0.6 g/ml. The powder with density above 0.6 g/ml was then mixed with 1% graphite powder and pilled to 3/16th inch by 3/16th inch cylinders having an apparent density of 1.10 to 1.15 g/ml.

Hardness was such that the pills could be broken in two by a force of 2 to 3 pounds on a knife edge pressing against the side perpendicular to the lengthwise axis.

The pilled catalyst was separated into two portions, one of which was not impregnated and the other of which was impregnated with an aqueous solution of rubidium carbonate of such volume and concentration that the pilled catalyst was covered by the aqueous solution and after removal of the water by evaporation under infrared light, the dried catalyst composition contained 4% by weight of rubidium carbonate. Both of these catalysts were examined by a procedure described hereinafter in Example 12 and the catalyst prior to the incorporation of the rubidium produced methanol in 100% yield with no detectable byproducts or higher alcohols. However, that which was impregnated with rubidium and tested under identical conditions of gas composition, gas flow, temperatures and pressures gave a product containing as much as 8% higher alcohols. These data are not recorded in the table subsequently presented but tests were made as described in the example accompanying that table.

EXAMPLE 2

A catalyst was prepared in a manner similar to that described in Example 1 with the exception that the composition comprised two mols of copper, two mols of zinc, two mols of manganese, 0.025 mols of cobalt and no moderator such as rubidium, potassium, cesium or other alkali metal. There was however a stabilizer comprising magnesium oxide present to the extent of 10% of the total oxides previously described. Precipitation, calcining, washing and pelletizing was all performed as called for in Example 1. This catalyst was evaluated as will be subsequently described in Example 12 and because of the absence of alkali it gave relatively high methanation and relatively low higher alcohols production. This is shown as Test 1 in the tabulation and descriptive matter relative to the test is given in the notations accompanying the tabulation.

EXAMPLE 3

A catalyst was prepared exactly as described for Example 2 except that a 4% quantity of potassium carbonate was added to the finally pilled catalyst before evaluation. This catalyst produced relatively large quantities of methane and is described in Tests 2 and 3 of the accompanying table together with notes pointing out and distinguishing this catalyst from catalysts made by our preferred procedures.

EXAMPLE 4

This catalyst was made similarly to that described in Example 3 and was evaluated and is reported as Test 4 in the tabulation. Of particular noteworthiness is the fact that the methane formation is unacceptably high being 5.6% of the carbon monoxide which is converted. It will be recalled that the formation of methane is harmful not only in itself but even more harmful in that during the purging to remove unwanted gases from the recycling gas the removal of the methane takes along with it at least two additional volumes of the desirable carbon monoxide and hydrogen.

EXAMPLE 5

This is the description of the manufacture of the catalyst used in Tests 5, 6 and 7. This catalyst is similar to that described in Example 4 with the exception that an identical weight quantity of rubidium is used instead of the potassium specified in Example 4. Two more things are noteworthy in this test, specifically that the rubidium decreases very substantially the amount of methane that is formed being approximately 40% to 50% less but of even more significance is the fact that the production ratio of water-free alcohol has been increased very substantially, by about 60%. The results of testing of the catalyst of this example are shown as Tests 5, 6 and 7 in the tabulation.

EXAMPLE 6

The catalyst prepared in this example is identical to that prepared in Example 5 with the exception that instead of the use of rubidium, cesium in like weight percent is used. The results of these tests are shown as Test 8 and 9 of the table accompanying Example 12. Again there are two very significant differences between Tests 8 and 9 and the earlier tests in which potassium was the moderator in that there is again substantially less methanation and an increase in alcohols production even above that obtained with the rubidium.

EXAMPLE 7

The catalyst of Example 7 was prepared exactly the same as the catalyst in Example 6 including the fact that the moderator was cesium. The purpose of these data and this example is to simply confirm data reported for Example 6 which is that methanation is extremely low and productivity is extremely high exceeding that of other catalysts under identical synthesis conditions.

EXAMPLE 8

This catalyst was prepared according to the same procedure described for the preceding examples however different ingredients were called for. These ingredients were as follows: four mols of copper, one mol of zinc, 3 mols of manganese, 0.2 mols of cobalt, the stabilizer was coprecipitated chromic oxide to the extent of 10-weight percent on the basis of all other oxides, and the moderator was 4% potassium as potassium carbonate. What is noteworthy is this example is the very high loss of synthesis gas to methane this being the highest methanation of any of the tests in the tabulation. The fact that the methanation was high would make for a higher temperature of catalytic reaction and this accounts very likely for the higher productivity. However the higher productivity was obtained at the high cost of the conversion of synthesis gas to methane. These data are reported as Tests 12 and 13 in the subsequent tabulation in Example 12.

EXAMPLE 9

Example 9 represents a catalyst prepared similarly to that described in Example 8. The variation in this example is that the moderator was 2% rubidium and 2% potassium comprising a mixture added in the same way as has been the practice in the previous examples. What is noteworthy in this example is that the methanation was high as characteristic of the potassium moderated catalyst but the productivity was the highest of any experienced to this point. It is evident that there are characteristics of the mixed moderators which are valuable for commercial adaptation and utilization. This test is number 14 of the tabulation in Example 12.

EXAMPLE 10

This example and the following example are to show effect of two important variables. First is the indication of the effect of differences in pressure on the reaction and the second effect is the difference in the amount of rubidium added to the catalyst. Both catalysts in Examples 10 and 11 were prepared similarly and with the exception of the rubidium content and were prepared as was described for the procedure in Example 8. What is notable in the catalyst of Example 10, the catalyst containing 4% rubidium and operating at 3500 psi, is the very sharp increase in the amount of total alcohols produced at the higher pressure. The results are noteworthy that methanation is relatively low despite the fact that the production rate is unsually high which would make for higher temperatures conducive to the formation of more methane.

EXAMPLE 11

The catalyst used in Example 11 is the same as that of Example 10 with the exception, as was pointed out in Example 10, that the quantity of rubidium is the highest of any included in the examples. It will be noted that the quantity of methanation is essentially the same as that when 4% rubidium was used but the quantity of higher alcohols produced was increased by about 25%. These data are all presented in Test 16 in the tabulation of the Example 12.

Catalyst Variations

The catalyst composition of Example 8 can be modified by alterations which achieve specific desirable objectives in the catalyst when it is used in the synthesis operation. For example, instead of the copper quantity called for in this example, one can increase the amount of copper to achieve a lower temperature light off. This however will introduce the tendency for increased methanation and if one is willing to sacrifice lower light off temperature for a minimization of methanation then the copper quantity is reduced. Copper proportion can be modified to achieve these two objectives.

Instead of the zinc proportion as called for in Example 8, one can increase the amount of zinc with the concommitant tendency to increase the amount of higher alcohols. Contrary to the effect with copper, increasing zinc does not increase the tendency of methanation so that zinc can be increased without a severe methanation or hydrocarbon penalty. Zinc does not have a strong tendency for the production of higher alcohols so its quantity is limited by the fact that it tends to increase the temperature at which the catalyst must be lighted off and operated. This also does not have the alcohol production qualities of per unit of time or per unit volume that is characteristic of the copper-bearing catalyst. Because of these two characteristics of zinc and copper the customary higher alcohols catalyst would usually contain a higher proportion of zinc than of copper.

It will be noted that the manganese content of this catalyst is equivalent on a molar basis to both that of copper and zinc. The manganese content however can be varied to increase the manganese and thereby achieve the greater tendency for higher alcohols production but usually at the expense of catalyst activity and of increased methanation. Furthermore, decreasing the manganese content will reduce the higher alcohols fraction but usually will also effect an increase in catalyst activity. As a consequence the quantity of manganese must be carefully chosen and is usually at a lower level than either the copper or the zinc particularly much lower than the zinc level.

Cobalt is added to increase the tendency for higher alcohols formation particularly ethanol. It will be noted that the cobalt quantity in this example is two tenths of a mol on the basis of 6 mols total of manganese, copper and zinc. The quantity or proportion of cobalt can be increased but this usually is at the expense of higher methanation and difficulty of controlling the reaction temperature and efficiency. The quantity of cobalt is usually less than that of either copper, zinc or manganese. In addition, as a trade-off for the cobalt to produce higher alcohols, it must be recognized that it has an almost uncontrollable tendency for the production of methane and hydrocarbons. This is a well-known fact traced back to the days when the Fischer Tropsche Reaction was invented and practiced. This tendency is controlled by components yet to be described.

Instead of the cobalt, one can use palladium, ruthenium, rhodium, platinum and rhodium. Nickel and iron can also to a certain degree be employed using careful control of the quantities added and as will subsequently be pointed out, the quantity of moderator (alkali metal salt), added. It will be noted by those skilled in the art that all of these elements have a strong tendency toward the production of methane and hydrocarbons under the condition of normal operation of these catalysts. The next ingredient to be added is the control factor that has proved to be most effective for the minimization of methane and the avoidance of hydrocarbons.

In the paragraph just above a "moderator" is added to the catalyst to avoid unwanted reactions and products. By "moderator" is meant the tendency for selected alkaline elements to avoid or minimize the production of hydrocarbons and methane. Previously we described most of the elements as being catalytic elements and as having a tendency for methanation and hydrocarbon formation. To compensate for this the alkaline metals, oxides or salts are added either individually or in mixtures with cesium and rubidium always being a required component. These alkali metals can be added as carbonate, hydroxide, sulfate, phosphate, chromate, dichromate, acetate, formate and other water soluble salts.

The alkali metals have been described as being added from a solution to the finished catalyst pellets. Addition at this stage is not essential and the solution can be added during the densification or kneading stage described in Example 1. However it should be borne in mind that if the salt of the alkali metal is added to the kneading operation, the quantity required may very well exceed the quantity that is required when the salt is placed on the exterior of the granules or pellets.

The precipitation of the catalyst as described in Example 1 can be performed using not only the nitrate salts but also the sulfates, chlorides or other water soluble salts. The decision as to what salt to use is generally made on the basis of the quality of the catalyst produced and on the economics involved in the preparation. Nitrates usually are preferred because of their tendency toward minimization of contamination particularly because the anion may be highly objectionable.

The catalyst can be prepared not only by precipitation but also can be prepared by the mixing of the nitrate salts or oxides or carbonates in the proper proportions and then calcined to arrive at an intimate mixture of the calcined material. This is generally not a preferred procedure.

An inexpensive and quite often suitable but again an inferior catalyst to that prepared by precipitation, can be made by supporting the catalyst as oxides on an inert support such as fused silica, fused alumina or inert materials of this type. The procedure involves making a solution of the nitrates of the components to be used in the catalytic material, putting in this solution the support material and then drying and calcining the solids onto the support material in such a way that approximately 15 to 20% catalytic constituents will be on the surface relative to the total weight of the catalyst plus support.

Instead of the quantity of cesium and rubidium called for in the examples above, one can instead use lesser or greater quantities with the lesser quantities being preferred from an economic standpoint but sometimes larger quantities are justified on the basis of the types and quantities of alcohols produced and the minimization of methanation and hydrocarbon formation. Not only can the quantity of rubidium be modified but also instead of using rubidium carbonate, one can sometimes beneficially use rubidium sulfate because the sulfate ion is itself a methanation and hydrocarbon inhibitor. Also in addition to the use of rubidium one can substitute therefor cesium, and cesium plus rubidium, and cesium plus rubidium plus other alkalis as various salts mentioned previously in this specification.

The examples above called for either the use of alumina, chromia, or magnesia as stabilizers (these ingredients can also be promoters or moderators) in approximately 10% quantities. The quantity of stabilizer can be increased or decreased as necessary to achieve the stability and moderating effect desired. Instead of the chromia, magnesia or alumina previously mentioned one can use instead or together with them other refractory oxides or carbonates, hydroxides or hydroxides of the lanthanides, silica, titania, zirconia, tantalum, niobium and alkali earths, in addition to the magnesia previously stipulated.

Instead of the catalyst being pelleted it can be extruded, made into granules, or as previously described, put onto a granular form. It is also possible that it could suitably be put onto honeycomb structures which would have the advantage of minimizing pressure drop.

The following tabulation of data were obtained in an automated reactor system permitting the evaluation of a 10 gram sample of catalyst. The equipment was so designed that the pressure can be varied from 500 to 5,000 psi, the gas composition can be almost infinitely varied with respect to $H_2$, CO and $CO_2$ content. Flow rates permit space velocities from 5,000 to 100,000; temperatures can be varied from 100° F. to 800° F. All catalysts were reduced at temperatures of 200°–250° C. using a $H_2$ stream diluted to 2 to 5% in $N_2$ or $CO_2$ before use. Temperature, pressure and flow rates are all automatically controlled. Gaseous and liquid product analyses are by gas chromatograph or mass spectrometry or both.

TABLE

| Test | Temp (F.°) | Gas Inlet CO | Gas Inlet CO₂ | Gas Inlet H₂ | MEOH | Acetal-dehyde | ETOH | 2-PR | Propion-aldehyde | 1-PR | Isobu-tral dehyde | Methyl Ethyl Ketone | SECB | ISOB | NBUT | Amyls | Activity Total | Activity W.F. | % of CO Reacted Converted to Methane | S.V. | Pressure psi |
|---|---|---|---|---|---|---|---|---|---|---|---|---|---|---|---|---|---|---|---|---|---|
| 1 | 750. | 20. | 0. | 80. | 96.25 | 0.85 | 1.31 | 0.08 | 0.06 | 0.74 | 0.02 | 0.00 | 0.00 | 0.68 | 0.00 | 0.00 | 1.64 | 1.25 | 89. | 40000. | 2,500 |
| Catalyst AI.0-The composition of the catalyst is Cu 2 mols. Zn 2 mols. Mn 2 mols. Co 0.025 mols. Cr₂O₃ 0%. Al₂O₃ 0%. Rb 0%. K 0%. MgO 10% |
| 2 | 750. | 20. | 0. | 80. | 73.17 | 2.45 | 12.38 | 2.15 | 0.25 | 7.05 | 0.24 | 0.26 | 0.37 | 0.57 | 0.33 | 0.78 | .60 | .44 | 51. | 40000. | 2,500 |
| 3 | 750. | 15. | 0. | 85. | 80.02 | 2.18 | 8.05 | 1.59 | 0.21 | 5.47 | 0.26 | 0.30 | 0.00 | 0.97 | 0.34 | 0.61 | .56 | .46 | 49. | 40000. | 2,500 |
| Catalyst AI 4% K-The composition of the catalyst is Cu 2 mols. Zn 2 mols. Mn 2 mols. Co 0.025 mols. Cr₂O₃ 0%. Al₂O₃ 0%. Rb 0%. K 4%. MgO 10% |
| 4 | 750. | 15. | 0. | 85. | 74.05 | 1.84 | 8.83 | 1.92 | 0.13 | 9.30 | 0.50 | 0.34 | 0.00 | 1.73 | 0.48 | 0.86 | .84 | .51 | 56. | 40000. | 2,500 |
| Catalyst AI 4% K-The composition of the catalyst is Cu 2 mols. Zn 2 mols. Mn 2 mols. Co 0.025 mols. Cr₂O₃ 0%. Al₂O₃ 0%. Rb 0%. K 4%. MgO 10% |
| 5 | 750. | 20. | 1. | 79. | 70.89 | 2.25 | 12.85 | 2.02 | 0.13 | 8.97 | 0.37 | 0.25 | 0.00 | 1.53 | 0.39 | 0.34 | 1.12 | .83 | 41. | 40000. | 2,500 |
| 6 | 750. | 20. | 0. | 80. | 76.73 | 1.87 | 8.79 | 1.58 | 0.19 | 7.18 | 0.38 | 0.22 | 0.00 | 1.48 | 0.32 | 1.25 | 1.02 | .86 | 28. | 40000. | 2,500 |
| 7 | 750. | 15. | 0. | 85. | 81.80 | 0.99 | 7.16 | 1.20 | 0.15 | 6.05 | 0.29 | 0.26 | 0.00 | 1.37 | 0.35 | 0.38 | .86 | .76 | 30. | 40000. | 2,500 |
| Catalyst AI 4% Rb-The composition of the catalyst is Cu 2 mols. Zn 2 mols. Mn 2 mols. Co 0.025 mols. Cr₂O₃ 0%. Al₂O₃ 0%. Rb 4%. MgO 10% |
| 8 | 750. | 20. | 0. | 80. | 85.32 | 1.92 | 5.24 | 1.07 | 0.28 | 3.78 | 0.20 | 0.29 | 0.00 | 1.12 | 0.25 | 0.54 | 1.16 | .97 | 28. | 40000. | 2,500 |
| 9 | 750. | 15. | 0. | 85. | 86.36 | 1.67 | 4.92 | 0.88 | 0.23 | 3.83 | 0.17 | 0.32 | 0.00 | 1.11 | 0.21 | 0.29 | .88 | .78 | 37. | 40000. | 2,500 |
| Catalyst AI 4% Cs-The composition of the catalyst is Cu 2 mols. Zn 2 mols. Mn 2 mols. Co 0.025 mols. Cr₂O₃ 0%. Al₂O₃ 0%. Rb 0%. 4% Cs, 10% MgO |
| 10 | 750. | 20. | 0. | 80. | 83.03 | 1.65 | 5.85 | 1.10 | 0.19 | 5.10 | 0.29 | 0.25 | 0.00 | 1.44 | 0.26 | 0.83 | 1.08 | .93 | 22. | 40000. | 2,500 |
| 11 | 750. | 15. | 0. | 85. | 84.84 | 1.49 | 5.36 | 0.87 | 0.14 | 4.82 | 0.21 | 0.25 | 0.00 | 1.34 | 0.26 | 0.42 | .98 | .88 | 23. | 40000. | 2,500 |
| Catalyst AI 4% Cs-The composition of the catalyst is Cu 2 mols. Zn 2 mols. Mn 2 mols. Co 0.02 mols. Cr₂O₃ 0%. Al₂O₃ 0%. Rb 0%. MgO 10% Cs 4% |
| 12 | 750. | 20. | 0. | 80. | 74.80 | 1.89 | 14.63 | 0.90 | 0.43 | 5.33 | 0.04 | 0.22 | 0.39 | 0.59 | 0.62 | 0.18 | 1.18 | .89 | 72. | 40000. | 2,500 |
| 13 | 750. | 15. | 0. | 85. | 73.52 | 1.79 | 15.50 | 0.89 | 0.32 | 6.06 | 0.06 | 0.26 | 0.00 | 0.97 | 0.62 | 0.01 | 1.02 | .85 | 77. | 40000. | 2,500 |
| Catalyst UK4-The composition of the catalyst is Cu 4 mols. Zn 1 mol. Mn 3 mols. Co 0.02 mols. Cr₂O₃ 10%. Al₂O₃ 0%. Rb 0%. K 0% |
| 14 | 750. | 20. | 0. | 80. | 69.61 | 2.21 | 14.38 | 1.30 | 0.33 | 8.70 | 0.13 | 0.34 | 0.00 | 1.63 | 0.72 | 0.64 | 1.42 | 1.16 | 72. | 40000. | 2,500 |
| Catalyst URK2-The composition of the catalyst is Cu 4 mols. Zn 1 mol. Mn 3 mols, Co 0.2 mols. Cr₂O₃ 10%. Al₂O₃ 0%. Rb 2%. K 2% |
| 15 | 750. | 20. | 0. | 80. | 78.04 | 1.15 | 9.08 | 0.69 | 0.29 | 6.88 | 0.11 | 0.31 | 0.17 | 2.07 | 0.54 | 0.65 | 2.52 | 2.18 | 40. | 40000. | 3,500 |
| Catalyst U4-The composition of the catalyst is Cu 4 mols. Zn 1 mol. Mn 3 mols. Co 0.2 mols. Cr₂O₃ 10%. Al₂O₃ 0%. Rb 4%. |
| 16 | 750. | 20. | 0. | 80. | 73.31 | 1.51 | 9.25 | 1.15 | 0.36 | 9.02 | 0.36 | 0.34 | 0.00 | 3.18 | 0.47 | 1.05 | 2.62 | 2.16 | 38. | 40000. | 3,500 |
| Catalyst U7-The composition of the catalyst is Cu 4 mols. Zn 1 mol. Mn 3 mols. Co 0.2 mols. Cr₂O₃ 10%. Al₂O₃ 0%. Rb 7% |

The above are representative data of a large mass of data which as been obtained in the research program generating this application. The above data have been selected as representative and also as establishing the following facts:

Note 1

In test 1 the given catalyst composition was evaluated with no added alkali moderator. It has all the other characteristics and components with the exception of the absence of the alkali. These data point out that methanation is relatively high, overall productivity is relatively high but the production of higher alcohols is to the extent of only about 3.75%. This is sharply in contrast to the data which will be commented on below.

Note 2

These tests, numbers 2 and 3, were made with different quantities of carbon monoxide in the gas stream and total absence of carbon dioxide. This catalyst contained the typical potassium alkali promoter which is well known in the art. Two things should be noted: first, is that the methanation is relatively high but not as high as in the previous test in which there is no alkali; the second is that the total production of alcohols is relatively low being less than one milliliter per milliliter of catalyst per hour.

Note 3

This note refers to Test 4 and has as its purpose the presenting of further evidence with regard to potassium as a promoter. It should be noted that methanation is relatively high and as in Test 2 and 3 total alcohols production is relatively low.

Note 5

This note refers to Tests 5, 6 and 7 and it should be noted from these that in Test 5 carbon dioxide was a component of the gas stream and in this test the methanation is relatively high when compared to Tests 6 and 7. However, the total productivity is relatively high and noteworthy is the fact that the production of higher alcohol fraction is also relatively high. Tests 6 and 7 reveal very low methanation, relatively high total alcohols productivity and a proportion of higher alcohols which is very good and a distribution of higher alcohols in the mixture which favors the production of propanol as partial replacement for ethanol. This is commercially very significant. The catalysts in Tests 5, 6 and 7 were all promoted with rubidium, a component which we are teaching is preferred to potassium because of the aforementioned attributes of low methanation and high total alcohols productivity.

Note 6

This notation refers to Tests 8 and 9 which is the same composition as the catalyst used in Tests 5, 6 and 7 including the fact that rubidium was the moderator and promoter. These data support the data obtained in Tests 5, 6 and 7 namely that methanation is low and production of total alcohols is high.

Note 7

This notation is in regard to Tests 10 and 11. This catalyst is similar to that used in Tests 5 through 9 with the exception that 4% cesium is used to replace 4% rubidium as a moderator and promoter for the catalyst. It will be noted that this is extremely low methanation being less than two and one-half percent and also has a high productivity rate for the total alcohols. The distribution of higher alcohols is very good when considering that the alcohols would be used for addition to gasoline as a solubilizer for the methanol.

Note 8

This note refers to Tests 12 and 13 which are made with a catalyst having an entirely different chemical composition than the catalyst used in the previous tests. In addition to the fact that the composition is changed, we have reverted to the use of potassium which is the moderator taught in prior art. It would be noted that the methanation in these tests is extremely high, being even higher than that in Tests 2, 3 and 4 reported above. Because of the different composition of the catalyst, it will also be noted that productivity however has reached a higher level than was true of these previously identified tests.

Note 9

This note refers to Test 14. This catalyst is the same composition as that used in Tests 12 and 13 with the exception that of the 4% potassium used in Test 14, 2% has been replaced with rubidium giving a moderator content of 2% rubidium and 2% potassium. Noteworthy items in this test are that methanation remains high but productivity is the highest of any reported test herein. Furthermore the proportion of higher alcohols in the total alcohols is excellent exceeding 30%. These factors with the exception of the methanation which can be corrected endows this catalyst with qualities of unusual interest for commercial exploitation.

Note 10

This note refers to Test 15 which catalyst is the same composition as that used in Test 14 with the exception that all of the potassium has now been replaced with rubidium. Furthermore the test was run at 3500 psi instead of the 2500 psi of previous tests. Noteworthy in this test is the relatively low methanation and extremely high total productivity of alcohols.

Note 11

This is in reference to Test 16 which is essentially the same catalyst as that used in Test 15 with the exception that the rubidium content has been increased from 4% to 7%. Noteworthy in this test is the relatively low methanation, the relatively high total productivity and the relatively high ratio of higher alcohols to total alcohols produced. Although the moderator in this test was all rubidium the data above with the mixed rubidium and potassium would indicate that replacement of at least part of the rubidium with potassium would be desirable. Also the replacement of some of the rubidium with cesium as well as potassium would also be extremely interesting from the viewpoint of low methanation, high productivity and excellent higher alcohols proportion as well as alcohols distribution.

Note 12

In the column headings in the table, Activity is expressed as ml alcohols produced per ml catalyst per hour.

Total means production including water.

W.F. means water free or anhydrous alcohols.

I claim:

1. A catalyst composition for use in the production of alkanols containing from 1 to 6 carbon atoms from a feed gas comprised of hydrogen and carbon monoxide, which is comprised of:
   (i) a mixture of the oxides of copper, zinc, and cobalt, which mixture may optionally contain manganese oxide;
   (ii) a stabilizer selected from the group consisting of aluminum oxide, cerium oxide, other lanthanides, zirconium oxide, titanium oxide, silicon dioxide, niobium oxide, tantalum oxide, chromic oxide, an alkaline earth metal oxide, an alkaline earth metal carbonate, and mixtures thereof; and
   (iii) at least one alkali metal salt or hydroxide, with the proviso that at least one of said salt or hydroxide be of rubidium or cesium.

2. A catalyst composition according to claim 1 which contains manganese oxide.

3. A catalyst composition according to claim 1 which contains from about 1 to about 50% by weight of stabilizer.

4. A catalyst composition according to claim 3 which contains from about 2 to about 14% by weight of stabilizer.

5. A catalyst composition according to claim 4 wherein the stabilizer is selected from the group consisting of aluminum oxide, cerium oxide, other lanthanides, chromic oxide, magnesium oxide, other alkaline earth oxides and mixtures thereof.

6. A catalyst composition according to claim 5 which contains from about 0.1 to 10% by weight of an alkali metal salt or hydroxide.

7. A catalyst composition according to claim 6 wherein the alkali metal salt is an alkali carbonate.

8. A catalyst composition according to claim 7 wherein the alkali carbonate is present in an amount from about 1 to 7% by weight.

9. A catalyst composition according to claim 8 wherein the stabilizer is magnesium oxide.

10. A catalyst composition according to claim 9 wherein the magnesium oxide is present in an amount of about 10% by weight.

11. A catalyst composition according to claim 10 which contains copper oxide, zinc oxide, manganese oxide, and cobalt oxide in the respective molar ratio and ranges of 0.1 to 4.0:0.1 to 4.0:0.1 to 4.0:0.01 to 4.0.

12. A catalyst composition according to claim 11 wherein the molar ratio of copper oxide:zinc oxide:manganese oxide:cobalt oxide is 2:2:2:0.025.

13. A catalyst composition according to claim 11 wherein the molar ratio of copper oxide:zinc oxide:manganese oxide:cobalt oxide is 4.0:1.0:3.0:0.2.

14. A catalyst composition according to claim 13 wherein the alkali carbonate is rubidium carbonate.

15. A catalyst composition according to claim 13 wherein the alkali carbonate is cesium carbonate.

16. A catalyst composition according to claim 14 wherein the alkali carbonate is a mixture of rubidium and potassium carbonates.

17. A catalyst composition according to claim 15 wherein the alkali carbonate is a mixture of cesium and potassium.

18. A catalyst composition according to claim 13 wherein the alkali carbonate is a mixture of rubidium and cesium carbonates.

19. A catalyst composition according to claim 18 wherein the alkali carbonate is a mixture of rubidium, cesium and potassium carbonate.

20. A catalyst composition according to claim 14 which contains about 4 percent by weight of rubidium carbonate.

21. A catalyst composition according to claim 16 which contains about 2 percent by weight of each of potassium carbonate and rubidium carbonate.

22. A catalyst composition according to claim 15 which contains about 4 percent by weight of cesium carbonate.

23. A catalyst compostion according to claim 17 which contains about 2 percent by weight of each potassium carbonate and cesium carbonate.

24. A catalyst composition according to claim 18 which contains about 2 percent by weight of each of rubidium carbonate and cesium carbonate.

25. A catalyst composition according to claim 19 which contains about 2 percent by weight of potassium carbonate, rubidium carbonate and cesium carbonate.

* * * * *